United States Patent
Soares et al.

(10) Patent No.: US 9,546,996 B2
(45) Date of Patent: Jan. 17, 2017

(54) SEQUENCING APPARATUS

(71) Applicant: BASE4 INNOVATION LTD, Cambridge (GB)

(72) Inventors: Bruno Flavio Nogueira de Sousa Soares, Cambridge (GB); Cameron Alexander Frayling, Cambridge (GB); Barnaby Balmforth, Cambridge (GB); Michele Amasio, Cambridge (GB)

(73) Assignee: BASE4 INNOVATION LTD., Cambridge (GB)

( * ) Notice: Subject to any disclaimer, the term of this patent is extended or adjusted under 35 U.S.C. 154(b) by 0 days.

(21) Appl. No.: 14/413,081

(22) PCT Filed: Jul. 9, 2013

(86) PCT No.: PCT/GB2013/051801
§ 371 (c)(1),
(2) Date: Jan. 6, 2015

(87) PCT Pub. No.: WO2014/009704
PCT Pub. Date: Jan. 16, 2014

(65) Prior Publication Data
US 2015/0204840 A1    Jul. 23, 2015

(30) Foreign Application Priority Data
Jul. 9, 2012    (GB) .................................. 1212135.6

(51) Int. Cl.
*G01N 33/487* (2006.01)
*H01Q 1/24* (2006.01)
(Continued)

(52) U.S. Cl.
CPC ........ *G01N 33/48721* (2013.01); *H01Q 1/243* (2013.01); *H01Q 1/521* (2013.01);
(Continued)

(58) Field of Classification Search
CPC ............................................... G01N 33/48721
See application file for complete search history.

(56) References Cited

U.S. PATENT DOCUMENTS

| 4,873,034 A | 10/1989 | Kono et al. |
| 6,267,872 B1 | 7/2001 | Akeson et al. |

(Continued)

FOREIGN PATENT DOCUMENTS

| DE | 101 57 070 A1 | 6/2003 |
| DE | 103 61 927 A1 | 7/2005 |

(Continued)

OTHER PUBLICATIONS

West et al., "Fabrication of Porous Polymer Monoliths in Microfluidic Chips for Selective Nucleic Acid Concentration and Purification", Methods in Molecular Biology, vol. 385, 2007, pp. 9-21.

(Continued)

*Primary Examiner* — Jill Warden
*Assistant Examiner* — Matthew Krcha
(74) *Attorney, Agent, or Firm* — Wenderoth, Lind & Ponack, L.L.P.

(57) ABSTRACT

The present invention provides an apparatus for analyzing the sequence of nucleotides in a nucleic acid sample, said apparatus comprising a substrate and a plurality of nanopores provided therein suitable for the passage of nucleic acid molecules therethrough; at least one sample holding chamber disposed upstream of the inlet of said nanopores, at least one detection window juxtaposed within or downstream of the outlet of each nanopore adapted to detect a property characteristic of one or more detectable elements associated with the nucleic acid as each nucleic acid molecule passes therethrough and a detector adapted to generate a data stream characteristic of the various detection events occur- (Continued)

ring in the detection window characterized in that the apparatus further comprises a means located within the sample holding chamber adapted to increase the local concentration of the nucleic acid sample adjacent the inlet of the nanopores relative to the bulk concentration thereof.

14 Claims, 1 Drawing Sheet

(51) Int. Cl.
- H01Q 1/52 (2006.01)
- H01Q 9/16 (2006.01)
- H01Q 9/26 (2006.01)
- H01Q 21/28 (2006.01)

(52) U.S. Cl.
CPC ............... *H01Q 9/16* (2013.01); *H01Q 9/265* (2013.01); *H01Q 21/28* (2013.01)

(56) References Cited

U.S. PATENT DOCUMENTS

| | | |
|---|---|---|
| 6,627,067 B1 | 9/2003 | Branton et al. |
| 6,746,594 B2 | 6/2004 | Akeson et al. |
| 6,972,173 B2 | 12/2005 | Su et al. |
| 6,982,165 B2 | 1/2006 | Yamakawa et al. |
| 7,238,477 B2 | 7/2007 | Su et al. |
| 2002/0182627 A1 | 12/2002 | Wang et al. |
| 2003/0036204 A1 | 2/2003 | Stark et al. |
| 2003/0104428 A1 | 6/2003 | Branton et al. |
| 2003/0207326 A1 | 11/2003 | Su et al. |
| 2005/0019784 A1 | 1/2005 | Su et al. |
| 2005/0023156 A1 | 2/2005 | Ramsey et al. |
| 2005/0034990 A1 | 2/2005 | Crooks et al. |
| 2005/0084912 A1 | 4/2005 | Poponin |
| 2005/0148064 A1 | 7/2005 | Yamakawa et al. |
| 2006/0066848 A1 | 3/2006 | Frankel |
| 2006/0147927 A1 | 7/2006 | Geddes et al. |
| 2006/0192115 A1 | 8/2006 | Thomas et al. |
| 2006/0238767 A1 | 10/2006 | Chen et al. |
| 2007/0153284 A1 | 7/2007 | Glazier et al. |
| 2007/0247620 A1 | 10/2007 | Koo |
| 2007/0273884 A1 | 11/2007 | Matsushita et al. |
| 2007/0275383 A1 | 11/2007 | Vocanson et al. |
| 2008/0025875 A1 | 1/2008 | Martin et al. |
| 2008/0037022 A1 | 2/2008 | Nishikawa et al. |
| 2008/0218761 A1 | 9/2008 | Nishikawa et al. |
| 2008/0239307 A1 | 10/2008 | Talley et al. |
| 2011/0162963 A1* | 7/2011 | Hibbs ............... G01N 33/48721 204/451 |
| 2012/0170034 A1 | 7/2012 | Van Dorpe et al. |

FOREIGN PATENT DOCUMENTS

| | | |
|---|---|---|
| EP | 1 645 628 | 4/2006 |
| JP | 2005-283556 | 10/2005 |
| WO | 2005/078415 | 8/2005 |
| WO | 2005/085806 | 9/2005 |
| WO | 2005/095927 | 10/2005 |
| WO | 2006/050257 | 5/2006 |
| WO | 2007/011389 | 1/2007 |
| WO | 2007/039852 | 4/2007 |
| WO | 2009/030953 | 3/2009 |
| WO | 2010/117470 | 10/2010 |
| WO | 2011/040996 | 4/2011 |
| WO | 2011/143340 | 11/2011 |

OTHER PUBLICATIONS

Ito et al., "Single-step concentration and sequence-specific separation of DNA by affinity microchip electrophoresis", 8th International Conference on Miniaturized Systems for Chemistry and Life Sciences, Sep. 26-30, 2004, Malmö, Sweden.
Ben McNally et al., "Optical Recognition of Converted DNA Nucleotides for Single-Molecule DNA Sequencing Using Nanopore Arrays", NANO letters, vol. 10, No. 6, Jun. 9, 2010, pp. 2237-2244.
Samir M. Iqbal et al., "Solid-state nanopore channels with DNA selectivity", Nature Nanotechnology, Nature Publishing Group, vol. 2, No. 4, Apr. 1, 2007, pp. 243-248.
Michael Zwolak et al., "Colloquium: Physical approaches to DNA sequencing and detection", Reviews of Modern Physics, American Physical Society, vol. 80, No. 1, Jan. 2, 2008. pp. 141-165.
Bala Murali Venkatesan, "Nanopore sensors for nucleic acid analysis", Nature Nanotechnology, vol. 6, No. 10, Sep. 18, 2011, pp. 615-624.
International Search Report and Written Opinion of the International Searching Authority issued Aug. 26, 2013 in corresponding PCT Application No. PCT/GB2013/051801.
Search Report issued Nov. 9, 2012 in GB Application No. GB1212135.6.
International Search Report and Written Opinion of the International Searching Authority issued Feb. 5, 2009 in International Application No. PCT/GB2008/050783.
Antoine Lesuffleur et al., "Periodic nanohole arrays with shape-enhanced plasmon resonance as real-time biosensors", Applied Physics Letters, Jun. 13, 2007, pp. 243110-1-243110-3, XP002511474.
Hagan Bayley et al., "Stochastic sensors inspired by biology", Nature, vol. 413, Sep. 13, 2001, pp. 226-230, XP002511333.
J. Aizpurua et al., "Optical Properties of Gold Nanorings", Physical Review Letters, vol. 90, No. 5, Feb. 7, 2003, pp. 057401-1-057401-4, XP002511334.
J. B. Heng et al., "The Electromechanics of DNA in a Synthetic Nanopore", Biophysical Journal, vol. 90, Feb. 2006, pp. 1098-1106, XP002511335.
Toshihiro Nakamura et al., "Enhancement of Dye Fluorescence by Gold Nanoparticles: Analysis of Particle Size Dependence", Japanese Journal of Applied Physics, vol. 44, No. 9A, Sep. 8, 2005, pp. 6833-6837, XP002511336.
Chuen Ho et al., "Electrolytic transport through a synthetic nanometer-diameter pore", Proceedings of the National Academy of Sciences of the United States of America, vol. 102, No. 30, Jul. 26, 2005, pp. 10445-10450, XP002511337.
M. Caterina Netti et al., "Confined Surface Plasmons in Gold Photonic Nanocavities", Advanced Materials, vol. 13, No. 18, Sep. 14, 2001, pp. 1368-1370, XP002511338.
S. O. Kucheyev et al., "Surface-enhanced Raman scattering on Nanoporous Au", Applied Physics Letters, Jul. 31, 2006, pp. 053102-1-053102-3, XP002511475.
Japanese Office Action issued Jan. 29, 2013 in Japanese Application No. 2010-523597, with English language translation.
Liu et al. "Biosensing based upon molecular confinement in metallic nanocavity arrays", Nanotechnology, 2004, vol. 15, pp. 1368-1347.
Stefan A. Maier, "Plasmonics: Fundamentals and Applications", Springer, 2007.
Examination Report issued Aug. 9, 2013 in European Application No. 08 788 753.5.
Kanglin Wang et al., "Single-Molecule Technology for Rapid Detection of DNA Hybridization Based on Resonance Light Scattering of Gold Nanoparticles", Chembiochem, vol. 10, No. 8, May 15, 2007, pp. 1126-1129.
Eugene Y. Chan, "Advances in Sequencing Technology", Mutation Research—Fundamental and Molecular Mechanisms of Mutagenesis, vol. 573, Feb. 25, 2005, pp. 13-40.

* cited by examiner

SEQUENCING APPARATUS

BACKGROUND OF THE INVENTION

Field of the Invention

The present invention relates to an apparatus for analysing the random sequence of monomer units in a polymer, for example a biopolymer. It is especially useful in determining the sequence of nucleotides in naturally occurring polynucleotides such as RNA, DNA or synthetic analogues thereof.

Description of the Related Art

Next generation sequencing of genetic material is already making a significant impact on the biological sciences in general and medicine in particular as the unit cost of sequencing falls in line with the coming to market of faster and faster sequencing machines. For example, our co-pending application WO 2009/030953 discloses a new fast sequencer in which inter alia the sequence of nucleotides (bases or base pairs) in a single or double stranded nucleic acid sample (e.g. naturally occurring RNA or DNA) is read by translocating the same through a nano-perforated substrate provided with plasmonic structures juxtaposed within or adjacent the outlet of the nanopores. In this device, the plasmonic structures define detection windows within which each nucleotide (optionally labelled) is in turn induced to fluoresce or Raman scatter photons in characteristic way by interaction with incident light. The photons so generated are then detected remotely, multiplexed and converted into a data stream whose information content is characteristic of the nucleotide sequence itself. This sequence can then be recovered from the data stream using computational algorithms embodied in corresponding software programmed into a microprocessor integral therewith or in a computing device attached thereto.

Another device for fast sequencing nucleic acids is described for example in U.S. Pat. No. 6,627,067, U.S. Pat. No. 6,267,872 and U.S. Pat. No. 6,746,594. In its simplest form this device employs electrodes, instead of plasmonic structures, to define the detection window in or around the outlet of the nanopore. A potential difference is then applied across the electrodes and changes in an electrical property of the ionic medium flowing therebetween, as a consequence of the electrophoretic translocation of the nucleic acid sample and associated electrolyte therethrough, is measured as a function of time. In this device, as the various individual nucleotides constituting the nucleic acid pass through the detection window they continuously block and unblock it causing 'blocking events' which give rise to characteristic fluctuations in current flow or resistivity. These fluctuations are then used to generate a suitable data stream for analysis as described above.

One problem encountered with both types of device described above is the need to improve the number of nucleic acid molecules flowing through a given nanopore in a given detection interval or the effective utilisation of the total number of nanopores in the same interval as these parameters are directly related to both the signal to noise ratio characteristic of the detector's output and the ease with which the data stream can be accurately processed. Whilst this problem can in theory partly be offset by progressively multiplexing larger and larger numbers of nano-perforations in a given unit area of substrate, the practical problems associated with creating such a high density of nanopores means that it would be most desirable to find a method of improving efficiency levels at current densities.

WO2011/143340 describes a method for sequencing a nucleic acid involving the steps of (1) dissociating a plurality of optically labelled oligonucleotides (e.g. molecular beacons) from a labelled nucleic acid as molecules thereof translocate through an array of nanopores and detectors and (2) detecting optical signals from the displaced oligonucleotides. Whilst regulation of the speed of translocation of the labelled nucleic acid molecules is discussed, the provision of a means for specifically increasing the local concentration thereof adjacent the inlet of the nanopores is not specifically discussed.

WO2010/117470 discloses a nanopore sequencing device comprising an array of nanopores in a substrate connecting upper and lower fluidic regions which are in turned linked to upper and lower fluid volumes. The upper and lower fluid regions are connected to the upper and lower fluid volumes by means of resistive openings whose roles are to minimise electrical cross-talk between the detectors associated with each nanopore in the array by slowing down the rate of translocation of the nucleic acid. Typically the resistive openings are channels of cross-section narrower than that of the space defining the fluidic regions. This device is thus concerned with solving different problem to that claimed in our invention and accordingly does not include a means for increasing the local concentration of the analyte.

WO2011/040996 teaches an ultrafast nanopore sequencing device for sequencing nucleic acids whose nucleotides are provided with acceptor labels. It uses excitable donor labels, e.g. quantum dots, located within or adjacent the inlet or outlet of the pore, to energetically excite the acceptor labels by energy transfer so that they emit fluorescence which can be detected. The device does not include a means for increasing the local concentration of the nucleic acid.

Methods in Molecular Biology 385 9-12 (2007) discusses the functionalization of porous polymer monoliths using for example amines, so that they are able to concentrate and purify oligonucleotides. Methods of making such monoliths are disclosed as is their use in microfluidic chips including microchannels. There is no discussion of using such monoliths in nanopore sequencers for the purposes of solving the problem addressed by the present invention. Rather the concern is to improve the sample preparation steps associated with conventional biological chips.

Royal Society of Chemistry Special Publication 159-160 (2005) exemplifies the single-step concentration of DNA in a microfluidic channel. The method employed involves contacting a solution of two single-stranded, 12-mers DNA analytes with a solution of a DNA-poly(N,N-dimethylacrylamide) having differing affinities for the two. On the basis of this differing affinity the two analytes were separated by electrophoresis. This is a completely different approach to that used in our invention and appears to be concerned with product purification rather than sequencing.

SUMMARY OF THE INVENTION

The rate at which nucleic acid molecules diffuse through a given nanopore by electrophoresis is mass transfer limited; i.e. it is controlled by the rate at which they diffuse from the sample bulk, to a region proximate to the inlet of the nanopore and then into the nanopore itself. Under normal circumstances this is determined by the concentration of the nucleic acid molecules in the bulk of the sample and the rates of diffusion and the mean free paths associated therewith. We have now found that by increasing the concentration of nucleic acid molecules adjacent to the inlet of the nanopores the rate of translocation can be significantly increased allowing more detections per unit time or more effective utilisation of the total number of nanopores in the device.

According to the present invention there is therefore provided an apparatus for analysing the sequence of nucleotides in a nucleic acid sample, said apparatus comprising a substrate and a plurality of nanopores provided therein suitable for the passage of nucleic acid molecules therethrough; at least one sample holding chamber disposed upstream of the inlet of said nanopores, at least one detection window juxtaposed within or downstream of the outlet of each nanopore adapted to detect a property characteristic of one or more detectable elements associated with the nucleic acid as each nucleic acid molecule passes therethrough and a detector adapted to generate a data stream characteristic of the various detection events occurring in the detection window characterised in that the apparatus further comprises a means located within the sample holding chamber adapted to increase the local concentration of the nucleic acid sample adjacent the inlet of the nanopores relative to the bulk concentration thereof.

Preferably the apparatus further comprises a means by which the data stream can be analysed to reveal the sequence of nucleotides or higher order nucleotide structures in the nucleic acid.

The term "nucleic acid" as used herein means a polymer of nucleotides. Nucleotides themselves are sometimes referred to as bases (in single stranded nucleic acid molecules) or as base pairs (in double stranded nucleic acid molecules) in an interchangeable fashion. Nucleic acids suitable for analysis by the device of the present invention are typically the naturally-occurring nucleic acids DNA or RNA or synthetic versions thereof. However the method can also be applied if desired to analogues such as PNA (peptide nucleic acid), LNA (locked nucleic acid), UNA (unlocked nucleic acid), GNA (glycol nucleic acid) and TNA (threose nucleic acid). The nucleic acids themselves in turn suitably comprise a sequence of at least some of the following nucleotides: adenine (A), cytosine (C), guanine (G), thymine (T) and uracil (U) 4-acetylcytidine, 5-(carboxyhydroxylmethyl)uridine, 2-O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentenyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine and 2-O-methyluridine. Especially suitable nucleic acids are on the one hand naturally mammalian DNA or RNA most suitably of all being human DNA or RNA and on the other the DNA or RNA characteristic of well known pathogens in the human body, foodstuffs, drinking water and the like.

Typically, the length of the target nucleic acid sequence is expressed in terms of the number of nucleotides it contains. For example, the term "kilobase" (kb) means 1000 nucleotides whilst "megabase" (Mb) means 1,000,000 nucleotides. The target nucleic acid used in the method of the present invention can in principle contain any number of nucleotides up to and including the number typically found in a human or other mammalian gene. However the method of the present invention is also applicable to smaller oligonucleotide fragments (e.g. fragments of a human gene) which are at least 10 bases (for single stranded nucleic acids) or base pairs (for double stranded nucleic acids) long, more typically at least 20, 30, 40, 50, 60, 70, 80, 90, 100, 500 or more bases/base pairs long or 1 kb, 2 kb, 5 kb, 10 kb, 20 kb, 50 kb, 100 kb, 250 kb, 500 kb or up to 1 Mb or more long. The nucleic acid sample itself may be derived directly or indirectly from any available biological sample including but not limited to materials such as blood, sputum or urine. The apparatus of the present invention can analyse both single- and double-stranded nucleic acids although it will be appreciated that in certain cases it will be preferable to analyse single-stranded nucleic acids especially single-stranded polynucleotides such as DNA or RNA.

DETAILED DESCRIPTION OF THE INVENTION

Figure 1:
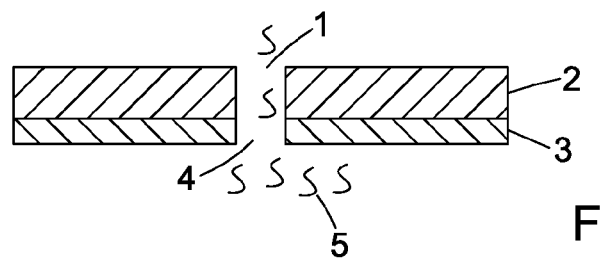
FIG. 1 schematically illustrates an example of the means to increase the local concentration of the nucleic acid in the sample holding chamber according to the first and second aspects of the apparatus of the present invention.

In a first aspect of the apparatus of the present invention, the means for locally concentrating the nucleic acid adjacent the inlet of the nanopores comprises a plurality of one or more different structures adapted to bind physically, chemically or biologically and in a reversible fashion to the nucleic acid molecules in the sample. The reversible nature of this binding can then, for example, be actively incorporated into a feedback loop where effectively the nanopore 'calls' for a nucleic acid molecule as and when it needs it. Such structures may include active surfaces such as a metal or metal oxide film on the substrate which can be nano-structured and/or chemically modified to promote reversible adherence thereto. Alternatively, adherence can be achieved by electrostatic charging of the substrate adjacent the nanopores or a coating thereon. Such charging can be fine tuned opening up the possibility of a highly controlled collection and release of the nucleic acid molecules. In yet another embodiment, a plurality of biological probes may be attached to the substrate or onto an element adjacent or substantially adjacent to the inlets of the nanopore. For example, such probes may be attached to the surface of the substrate in the immediate vicinity of the nanopores or on a separate surface which is located nearby. In one embodiment, such biological probes are comprised of short, single polynucleotide strands, typically up to 100, preferably up to 50, nucleotides long, which are able to hybridise with the nucleic acid sample at sites thereon where the sequences of nucleotides in the probe and sample are complimentary. In attaching the probe to the surface of the substrate or element it is preferred that the latter are modified to facilitate binding of the former thereto. For example, the substrate or element may first be covered with a reactive organic polymer which can chemically bind to the probes. Suitable organic polymers include polyacrylates, polymethacrylates, polycarbonates, functionalised polystyrenes, e.g. sulfonated polystyrenes, polymer polyols, polyethylene glycols and the like. It is also preferred that the surface of the substrate is treated to make it chemically reactive for said reactive organic polymer e.g. by silination using a reactive silicate or silicon tetrachloride in the case where the substrate or element is fabricated from silicon, silicon oxide or silicon carbide. The probe may thereafter be attached to the polymer using known methods.

In one embodiment of the above, the number of structures attached to the substrate or the element within a sample chamber zone corresponding to a hemisphere around each nanopore of diameter d, (where d is a distance corresponding to half the average distance between adjacent nanopores) corresponds to at least twice, preferably at least ten times, most preferably at least fifty times the number of nucleic acid molecules in the same volume of the bulk nucleic acid sample to be analysed. In another embodiment, the sample chamber zone used corresponds to a hemisphere around each nanopore of diameter d' where d' is a distance corresponding to less than 50%, preferably less than 25% of the mean free path of the nucleic acid molecule in a typical nucleic acid sample at 25° C. with d' being no less than twice preferably no less than five times the average diameter of the nanopores themselves.

In this first aspect of the apparatus the sample chamber is typically first charged with the bulk nucleic acid sample solution and then treated to cause the nucleic acid molecules contained therein to attach to the structures. Methods for doing this are well known in the art and in the case of biological probes suitably involve the well-known technique of hybridisation. This attachment process can be repeated multiple time if necessary until at least 30% preferably at least 50% preferably substantially all of the structures have been utilised.

In a second aspect of the apparatus of the present invention the sample chamber is divided into at least two sub-chambers separated by a membrane which is permeable to the nucleic acid molecules in the sample. The bulk nucleic acid sample is then placed in the sub-chamber remote from the nanopores (the 'first sub-chamber') and the nucleic acid molecule caused to diffuse through the membrane into the sub-chamber adjacent the nanopores (the 'second sub-chamber') by applying a potential difference across the membrane. This in effect concentrates the nucleic acid molecules in the second sub-chamber and counteracts any back-diffusion caused by osmotic pressure. Once concentration is complete a potential difference is then applied across the substrate causing the high concentration of nucleic acid molecules located in the second sub-chamber (relative to the first sub-chamber) to translocate through the nanopores. Thereafter, the translocating nucleic acid molecules are detected and the corresponding data stream analysed by subsequent computer processing as explained below. In a preferred embodiment of this second aspect, the membrane is adapted to be permeable to the nucleic acid molecules only in the direction from the first to the second sub-chambers. The membrane can for example be fabricated from an array of highly selective organic pores typically found in biological material such as cells. If so desired the applying of the potential differences across the membrane and the substrate can be synchronised so that in effect the nanopore calls for more nucleic acid when it needs it.

The present invention is now illustrated by FIGS. 1 to 4 which schematically illustrate four examples of the means to increase the local concentration of the nucleic acid in the sample holding chamber according to the first and second aspects of the apparatus of the present invention described above.

In FIG. 1, nanopore 1 in substrate membrane 2 is provides with an electrostatic charging layer 3 juxtaposed on 2 on the inlet side of 1 adjacent to the sample holding chamber (not shown). Individual nucleic acid molecules 4 are attracted to from a local concentration thereof at 5 and then individually caused to flow through 1 by electrophoresis to the outlet side of 1 where they pass through a detection window (not shown) arising from gold plasmonic particles located on the outlet face of 2 around 1.

Figure 2:
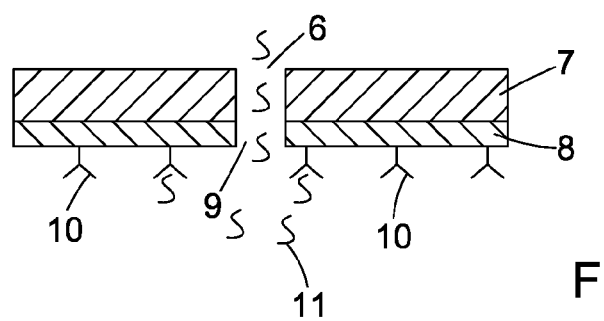
FIG. 2 schematically illustrates an example of the means to increase the local concentration of the nucleic acid in the sample holding chamber according to the first and second aspects of the apparatus of the present invention.

In FIG. 2, nanopore 6 in substrate membrane 7 is provided with a polyethylene glycol (PEG) layer 8 juxtaposed on 7 on the inlet side of 6 adjacent to the sample holding chamber (not shown). Attached to 8 are oligonucleotides 10 adapted to collect and hybridise to nucleic acid molecules 11 from the sample bulk solution. Individual nucleic acid molecules 9 are then caused to flow through 6 by electrophoresis to the outlet side of 6 where they pass through a detection window (not shown) arising from gold plasmonic particles located on the outlet face of 7 around 6.

Figure 3:
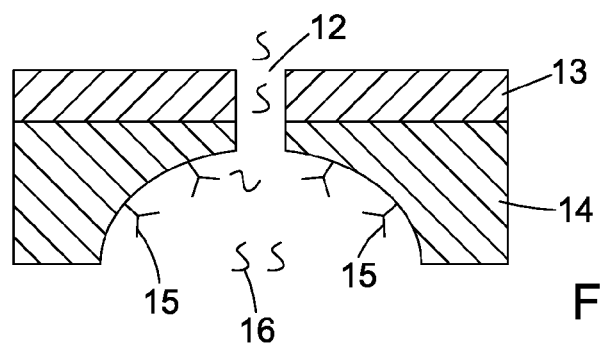
FIG. 3 schematically illustrates an example of the means to increase the local concentration of the nucleic acid in the sample holding chamber according to the first and second aspects of the apparatus of the present invention.

FIG. 3 is a variation of the configuration shown in FIG. 2 in which substrate 13 is provided on its nanopore inlet side with a hemispherical chamber 14 to which the oligonucleotides 15 are attached as described above. By this means a local concentration of nucleic acid molecules can be established in 14 at 16 before flowing through nanopore 12 to the detection window as described above.

Figure 4:
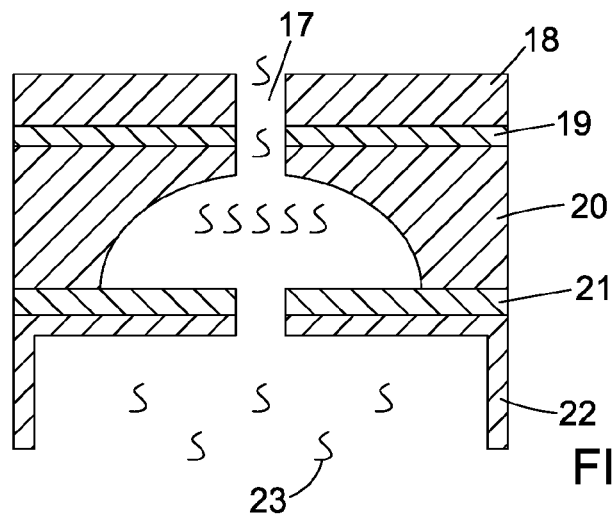
FIG. 4 schematically illustrates an example of the means to increase the local concentration of the nucleic acid in the sample holding chamber according to the first and second aspects of the apparatus of the present invention.

FIG. 4 is a two-stage variation of the configuration shown in FIG. 3 in which electrodes 19 are sandwiched between the substrate 18 and the hemispherical chamber 20 in which the nucleic acid molecules 23 are concentrated. In this embodiment the lower face of 20 is attached to the upper face of a second nanoperforated substrate 21 which is further attached to the upper walls of sample holding chamber 22. In this embodiment the nucleic acid molecules undergo intermediate concentration in 20 before passing through nanopore 17 to the detection window described above.

In the apparatus of the present invention, the nucleic acid molecules in the sample having the necessary detectable elements are analysed by translocation through the nanopores into the detection windows. These detectable elements can comprise the nucleic acid's constituent nucleotides themselves and/or moieties within them (in the case of the electrical or Raman scattering methods) or marker moieties selectively bound to one or more of these nucleotides (as in the case where fluorescent marker moieties are employed). In an embodiment of the apparatus employing the detection of photons, e.g. fluorescence or Raman scattering, the detection window is defined by a localised electromagnetic field generated by plasmon resonance. The interaction between this electromagnetic field, the detectable elements and incident electromagnetic radiation impinging on the detection window is then used to generate an increased level of fluorescence or Raman scattering which can be easily detected and analysed.

As mentioned above, an example of this approach can be found in our WO 2009/030953 the contents of which are incorporated herein by reference. Here, the detection window is defined by one or more metallic moieties, fabricated from gold or silver, capable of undergoing plasmon resonance when stimulated by incident electromagnetic radiation from a coherent source such as a laser. This plasmonic resonance generates the strong localised electromagnetic field through which the nucleic acid molecules and hence the nucleotides and detectable elements pass. The exact geometry of these metallic moieties determines the geometry of the detection window this electromagnetic field gives rise to and hence affects the nature of the interaction with the detectable elements. For example, the geometry of the detection window can be chosen so as to be optimised for increased photon emission, rather than for lateral localisation. This is achieved by producing detection windows with a greater z length (the dimension along which the nucleic acid translocates), and modifying their geometry appropriately in the x and y dimensions in order to ensure their peak plasmonic resonance frequency is maintained at a desired wavelength. Preferably, the detection window is sized so that the length in the z dimension is from 1 to 100 preferably from 10 to 50 nanometers.

The signal generated by the interaction of the detectable elements and the electromagnetic field can be detected by a detector such as a photocounter in the case of fluorescence or a spectrometer in the case of Raman scattering. The output of such a device will typically be an electrical signal characteristic of the sequence of nucleotides in the nucleic acid.

In a second preferred embodiment the detection window is defined by one or more pairs of electrodes located within or adjacent to the outlet of each nanopore and a potential difference associated therewith. Further details concerning this arrangement can be found in the above-mentioned US patents the contents of which are incorporated by reference. As mentioned above, here the characteristic data stream and/or signal is generated by fluctuations in an electrical property of the detection window and/or its contents (e g changes in voltage, resistance or current flow occasioned by the detectable element blocking or enabling the flow of ions in the nucleic acid's associated translocation medium between electrodes). Preferred translocation media include aqueous alkali metal electrolytes such as an aqueous potassium or sodium halide, nitrate or sulphate solution.

In both of these manifestations of the apparatus, the nano-perforated substrate may either be fabricated from an inorganic insulator or from organic or biological material. Preferably the nano-perforated substrate is an inorganic insulator such as a silicon carbide wafer. Typically, the nanopore is between 1 nm and 100 nm in diameter preferably 1 nm to 50 nm, 2 nm to 30 nm, 5 nm to 20 nm or 5 nm to 15 nm. The nucleic acid molecules are suitably caused to translocate through the nanopores by electrophoresis. Passage through the nanopore ensures that the nucleic acid translocates in a coherent, linear fashion so that it emerges from the outlet thereof in a nucleotide by nucleotide fashion enabling the detectable elements to be detected in order.

Likewise in both embodiments the apparatus may suitably employ multiple detectors. For example, an array of detector/detection windows pairs may be used with each detector being arranged to detect photons or an electrical property generated using its paired detection window. For photon generating events, suitable detectors may include but are not limited to photo-detectors such as photon counters, photo-multipliers, single photon avalanche diodes and the like.

The data stream which is provided by the photo-detectors or the electrical measurements is suitably a signal which can be analysed by software comprised of the relevant algorithms loaded on a microprocessor or the like suitably integral with the apparatus itself or part of a remote or separate computer connected to the apparatus by known conventional techniques including but not limited to across the Internet. The data stream itself and/or the sequence data recovered therefrom can be used to sequence de novo nucleic acids whose structure is completely unknown or for comparative purposes e.g. by aligning the sequence against sequence data of a known reference. In such latter applications it is preferred not to detect every nucleotide systematically but rather to identify certain useful higher order structures e.g. methylated CPG sites, G4 Quadruplexes and the like which can provide useful therapeutic insights when for example compared across a population of subjects able to provide sequence data in respect of essentially the same nucleic acid. Here the sequence data so obtained can be likened to a barcode able to identify similarities and differences without the need to go to the time and expense of carrying out a complete sequencing which can be very costly and time-consuming computationally. The apparatus of the present invention is also especially useful for concentrating, detecting and identifying strains of pathogens in samples which can be of human or animal origin on the one hand or foods and commodities such as drinking water on the other hand. This is of great use in tracking down their origin, mutation history and epidemiology.

The invention claimed is:

1. An apparatus for analysing the sequence of nucleotides in a nucleic acid sample, said apparatus comprising a substrate and a plurality of nanopores provided therein suitable for the passage of nucleic acid molecules therethrough; at least one sample holding chamber disposed upstream of the inlet of said nanopores, at least one detection window juxtaposed within or downstream of the outlet of each nanopore adapted to detect a property characteristic of one or more detectable elements associated with the nucleic acid as each nucleic acid molecule passes therethrough and a detector adapted to generate a data stream characteristic of the various detection events occurring in the detection window characterised in that the apparatus further comprises a means located within the sample holding chamber adapted to increase the local concentration of the nucleic acid sample adjacent the inlet of the nanopores relative to the bulk concentration thereof, wherein the concentrating means comprises a plurality of one or more different physical, chemical or biological structures adapted to bind selectively and reversibly to the nucleic acid molecules each of which structures are located on the substrate or on an element adjacent to the inlets of the nanopore.

2. An apparatus as claimed in claim 1 characterised in that it further comprises a microprocessor programmed to analyse the data stream to reveal the sequence of nucleotides or higher order nucleotide structures in the nucleic acid sample.

3. An apparatus as claimed in claim 1 characterised in that the structures are selected from, nano-structured surfaces, electrostatically chargeable surfaces, surfaces which are able to bind chemically to the nucleic acid molecules or biological probes.

4. An apparatus as claimed in claim 3 characterised in that the number of structures attached to the substrate or the element within a sample chamber zone corresponding to a hemisphere around each nanopore of diameter d, (where d is a distance corresponding to half the average distance between adjacent nanopores) corresponds to at least twice, preferably at least ten times, most preferably at least fifty times the number of nucleic acid molecules in the same volume of the nucleic acid sample to be analysed.

5. An apparatus as claimed in claim 3 characterised in that the number of structures attached to the substrate or the element within a sample chamber zone corresponding to a hemisphere around each nanopore of diameter d' (where d' is a distance corresponding to less than 50%, preferably less than 25% of the mean free path of the nucleic acid molecule in a typical nucleic acid sample at 250 C with d' being no less than twice preferably no less than five times the average diameter of the nanopores themselves) corresponds to at least twice, preferably at least ten times, most preferably at least fifty times the number of nucleic acid molecules in the same volume of the nucleic acid sample to be analysed.

6. An apparatus as claimed in claim 1 characterised in that the one or more different physical, chemical or biological structures include a metal or a metal oxide film which promotes reversible adherence thereto to enable the nanopore to call for a nucleic acid molecule and at that time it is required for translocation therethrough.

7. An apparatus as claimed in claim 1 characterised in that the sample chamber is divided into at least two sub-chambers separated by a membrane which is permeable to the nucleic acid molecules in the sample.

8. An apparatus as claimed in claim 7 characterised in that two sub-chambers comprises first and second sub-chambers respectively remote from and adjacent to the nanopores the first sub-chamber being adapted to receive the nucleic acid sample and the second sub-chamber being adapted to allow nucleic acid molecules to be concentrated therein.

9. An apparatus as claimed in claim 8 characterised in that it further comprises means for applying a potential difference across the membrane to cause the nucleic acid molecules to flow from the first to the second sub-chamber by electrophoresis.

10. An apparatus as claimed in claim 7 characterised in that the membrane is only permeable to the nucleic acid molecules in the direction from the first to the second sub-chamber.

11. An apparatus as claimed in claim 1 characterised in that the detection window comprises plasmonic structures adapted to induced fluorescence or Raman scattering in the detectable elements passing therethrough.

12. An apparatus as claimed in claim 11 characterised in that it further comprises a detector for detecting fluorescence or Raman scattered photons as a function of time.

13. An apparatus as claimed in claim 1 characterised in that the detection window comprises electrodes and a means for measuring an electrical property characteristic of the medium issuing from the outlet of the nanopore pore and flowing therebetween.

14. An apparatus as claimed in claim 1 characterised in that it comprises a microprocessor integral therewith programmed with software including a data base of reference sequences.

* * * * *